United States Patent
Leugers

(10) Patent No.: US 9,995,626 B1
(45) Date of Patent: Jun. 12, 2018

(54) MICRO-FLUORESCENCE CAPABLE MICRO-RAMAN SPECTROMETER

(71) Applicant: Dow Global Technologies LLC, Midland, MI (US)

(72) Inventor: Mary Anne Leugers, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 108 days.

(21) Appl. No.: 14/884,882

(22) Filed: Oct. 16, 2015

Related U.S. Application Data

(60) Provisional application No. 62/098,107, filed on Dec. 30, 2014.

(51) Int. Cl.
*G01J 3/18* (2006.01)
*G02B 21/00* (2006.01)
*G01J 3/44* (2006.01)
*A61B 5/00* (2006.01)

(52) U.S. Cl.
CPC .............. *G01J 3/18* (2013.01); *A61B 5/0068* (2013.01); *G01J 3/4406* (2013.01); *G01J 3/4412* (2013.01); *G02B 21/0024* (2013.01); *G02B 21/0032* (2013.01)

(58) Field of Classification Search
CPC .... G01J 3/44; G01J 3/4406; G01J 2003/1885; G01J 3/18; G01J 3/4412; G02B 21/0032; G02B 21/0024; A61B 5/0068
See application file for complete search history.

(56) References Cited

U.S. PATENT DOCUMENTS

| | | | | |
|---|---|---|---|---|
| 3,390,604 A | * | 7/1968 | Makabe ............... | G01J 3/18 356/328 |
| 3,822,941 A | * | 7/1974 | Roche ................. | G01J 3/06 356/325 |
| 4,718,764 A | * | 1/1988 | Fink ................... | G01J 3/12 356/328 |
| 4,775,234 A | * | 10/1988 | Shimomura ......... | G01J 3/02 250/339.07 |

(Continued)

OTHER PUBLICATIONS

CRAIC Technologies, "CRAIC ApolloTM Raman Spectrometer" [retrieved on Feb. 26, 2016]. Retrieved from the Internet: < URL: http://www.microspectra.com/products/apollo>.

*Primary Examiner* — Michael P Lapage
(74) *Attorney, Agent, or Firm* — McDonnell Boehnen Hulbert & Berghoff LLP

(57) ABSTRACT

A confocal microscope, operable to focus on any of a plurality of portions of a sample, is optically coupled to a light source and to a spectrograph module. When the confocal microscope focuses on a particular portion of the sample, the confocal microscope directs incident light from the light source to the particular portion and directs responsive light from the particular portion to the spectrograph module. The spectrograph module can be operated using a first diffraction grating having a first line density to obtain a Raman spectrum of the responsive light from the particular portion of the sample. The spectrograph module can also be operated using a second diffraction grating having a second line density that is less than the first line density to obtain a fluorescence or phosphorescence spectrum of the responsive light from the particular portion of the sample.

13 Claims, 4 Drawing Sheets

(56) References Cited

U.S. PATENT DOCUMENTS

| | | | | |
|---|---|---|---|---|
| 5,565,983 | A | * | 10/1996 | Barnard .................... G01J 3/02 356/328 |
| 5,905,571 | A | * | 5/1999 | Butler ....................... G01J 3/18 356/326 |
| 5,949,532 | A | * | 9/1999 | Schrof ...................... G01J 3/44 250/458.1 |
| 6,583,873 | B1 | * | 6/2003 | Goncharov ............... G01J 3/06 356/326 |
| 7,701,574 | B2 | * | 4/2010 | Johansen .................. G01J 3/18 356/328 |
| 2003/0030812 | A1 | * | 2/2003 | Marcus .................... H04N 3/36 356/445 |
| 2004/0246477 | A1 | * | 12/2004 | Moon ....................... G01J 3/02 356/300 |
| 2008/0030728 | A1 | * | 2/2008 | Nguyen .................... G01J 3/02 356/328 |
| 2009/0116008 | A1 | * | 5/2009 | Fukuda ............. G01N 21/6428 356/317 |
| 2010/0173228 | A1 | * | 7/2010 | Wallace ............. H01M 4/8605 429/532 |
| 2012/0033213 | A1 | * | 2/2012 | Yang ........................ G01J 3/02 356/326 |
| 2015/0294076 | A1 | * | 10/2015 | Treado .................. G01N 21/65 506/12 |
| 2015/0369666 | A1 | * | 12/2015 | Kostamovaara ....... G01N 21/65 356/301 |

* cited by examiner

MICRO-FLUORESCENCE CAPABLE MICRO-RAMAN SPECTROMETER

CROSS REFERENCE TO RELATED APPLICATION

This application claims priority to U.S. Provisional Application No. 62/098,107 filed on Dec. 30, 2014, the entirety of which is hereby incorporated by reference.

BACKGROUND

Unless otherwise indicated herein, the materials described in this section are not prior art to the claims in this application and are not admitted to be prior art by inclusion in this section.

Confocal spectroscopy generally involves using a confocal microscope to selectively direct incident light toward a particular portion of a sample to generate responsive light from the particular portion of the sample. The responsive light may be directed toward a light sensor via filters, diffraction gratings, or other optical elements so that the responsive light may be analysed to determine characteristics of the sample. To this end, intensities and corresponding wavelengths of the responsive light may be determined with respect to location within the sample.

Within the context of confocal Raman spectroscopy, the determined intensities and corresponding wavelengths may be used to identify vibrational or rotational energy levels excited by the incident light at various locations within the sample, thereby allowing materials or material phases present within the particular portion of the sample to be identified. Likewise, within the context of fluorescence or phosphorescence spectroscopy, the determined intensities and corresponding wavelengths may be used to identify electronic energy levels excited by the incident light at various locations within the sample, similarly allowing materials or material phases present within the particular portion of the sample to be identified.

SUMMARY

Example embodiments provide systems and methods for performing confocal Raman spectroscopy and confocal fluorescence or phosphorescence spectroscopy of a particular portion of a sample. Further, the embodiments may allow for collecting both a Raman spectrum and a fluorescence or phosphorescence spectrum of the (same) particular portion of the sample without moving the sample between different instruments. This may obviate the need to refocus upon the particular portion of the sample upon moving the sample between the instruments. The example systems and methods may facilitate collecting the Raman and fluorescence/phosphorescence spectra by using filters and/or diffraction gratings that are interchangeable without adjustment of the confocal optical elements of the system or the position of the sample.

In one example, a system includes a light source configured to emit incident light and a first diffraction grating having a first line density. The system further includes a second diffraction grating having a second line density, where the first line density is greater than the second line density. The system further includes a spectrograph module comprising a light sensor and a mount configured (i) to receive the first diffraction grating to provide a first mode of operation and (ii) to receive the second diffraction grating to provide a second mode of operation. The system further includes a confocal microscope optically coupled to the light source and the spectrograph module, where the confocal microscope is operable to selectively focus on any of a plurality of portions of a sample, such that when the confocal microscope focuses on a particular portion of the sample the confocal microscope directs the incident light from the light source to the particular portion of the sample and directs responsive light from the particular portion of the sample to the spectrograph module. In the first mode of operation the spectrograph module is operable to obtain a Raman spectrum of the responsive light using the first diffraction grating and in the second mode of operation the spectrograph module is operable to obtain a fluorescence or phosphorescence spectrum of the responsive light using the second diffraction grating.

In another aspect, an example method includes using a confocal microscope to focus on a particular portion of a sample. The method further includes directing, via the confocal microscope, incident light from a light source to the particular portion of the sample, thereby generating responsive light from the particular portion of the sample. The method further includes directing, via the confocal microscope, the responsive light from the particular portion of the sample to a spectrograph module. The spectrograph module comprises a light sensor and a mount configured to receive any of a plurality of different diffraction gratings having different respective line densities. The method further includes dispersing, by a first diffraction grating having a first line density, the responsive light toward the light sensor. The method further includes obtaining, by the spectrograph module, a Raman spectrum of the responsive light dispersed by the first diffraction grating. The method further includes dispersing, by a second diffraction grating having a second line density, the responsive light toward the light sensor. The first line density is greater than the second line density. The method further includes obtaining, by the spectrograph module, a fluorescence or phosphorescence spectrum of the responsive light dispersed by the second diffraction grating.

These as well as other aspects, advantages, and alternatives, will become apparent to those of ordinary skill in the art by reading the following detailed description, with reference where appropriate to the accompanying drawings.

DETAILED DESCRIPTION

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As noted above, both confocal Raman spectroscopy and confocal fluorescence/phosphorescence spectroscopy may be useful to identify or characterize materials or material phases present within a sample by identifying energy levels excited by light incident upon the sample. That is, in response to incident light, the sample may emit responsive light that has wavelengths that can reveal the excited energy levels. However, optical elements suitable for performing confocal Raman spectroscopy may differ from optical elements suitable for performing confocal fluorescence/phosphorescence spectroscopy.

One example of such an optical element is a diffraction grating, which is useful for dispersing (poly-chromatic) light according to wavelength so that constituent wavelengths of the light may be identified. For example, since confocal Raman spectroscopy may involve analysis of shorter wavelengths of the responsive light, a suitable diffraction grating may have high wavelength resolution but a lower high-end cut-off wavelength, since longer wavelengths may not be of interest. On the other hand, fluorescence/phosphorescence spectroscopy may involve analysis of longer wavelengths of the responsive light, so a suitable diffraction grating may have a higher high-end cut-off wavelength at the expense of lower wavelength resolution.

Figure 1:
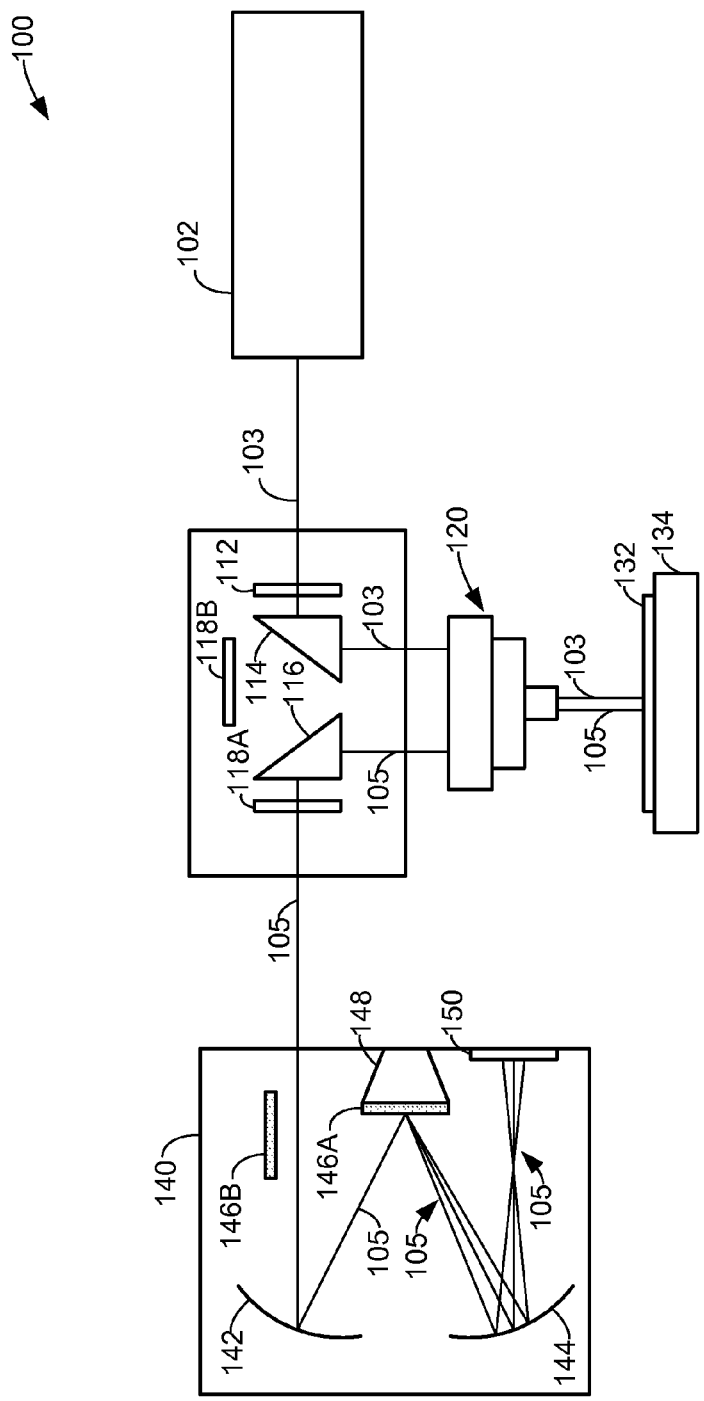
FIG. 1 illustrates an example system for collecting a Raman spectrum and fluorescence or phosphorescence spectra of a sample.

FIG. 1 illustrates an example system 100 for collecting Raman and fluorescence/phosphorescence spectra of a sample 132. The system 100 includes a light source 102, filters 112, 118A and 118B, light guides 114 and 116, a confocal microscope 120, a sample mount 134, and a spectrograph module 140. The spectrograph module 140 includes light guides 142 and 144, diffraction gratings 146A and 146B, a grating mount 148, and a light sensor 150.

The light source 102 may be configured to emit incident light 103 toward the filter 112 and/or the light guide 114. For example, the light source 102 may include one or more laser modules (e.g., a laser diode) configured to emit respective wavelengths of light. More specifically, the light sensor 102 may include a first laser module configured to emit light at a wavelength of 455 nanometers (nm), a second laser module configured to emit light at a wavelength of 532 nm, and a third laser module configured to emit light at a wavelength of 780 nm. Although laser modules may nominally emit a single wavelength, in practice, such laser modules may actually emit light having a non-zero bandwidth. In other examples, the light source 102 may include a broadband light source such as a xenon continuous wave lamp or a flashlamp. Other examples are possible.

The filter 112 (e.g., a monochromator) may be configured to receive the incident light 103 from the light source 102. The filter 112 may include a (i) prism or a diffraction grating configured to disperse various wavelengths of the incident light 103 and (ii) a slit or aperture aligned so as to selectively allow a band of desired wavelengths to pass through the slit or aperture. For example, the filter 112 may be used to narrow the bandwidth of wavelengths of the incident light 103 that is provided to the light guide 114, to better emulate an ideal monochromatic light source.

In other examples, the filter 112 may be an absorptive filter, or preferably, a dichroic filter. Such a dichroic filter may include multiple material layers of various refractive indices deposited upon glass or quartz, for example. The dichroic filter may cause destructive interference of certain wavelengths of incident light 103, thereby acting to attenuate transmission of those wavelengths of light. Conversely, the dichroic filter may allow transmission of other wavelengths of incident light 103 without significant attenuation.

The light guide 114 may be configured to receive the incident light 103 from the filter 112. The light guide 114 may include one or more reflectors or mirrors, however any optical elements configured to redirect the incident light 103 toward the confocal microscope 120 may be included as part of the light guide 114.

The confocal microscope 120 may be optically coupled to the light source 102 (e.g., via the light guide 114 and/or the filter 112) and the spectrograph module 140 (e.g., via the filters 118A or 118B and the light guide 116). The confocal microscope 120 may be operable to selectively focus on any of a plurality of portions of the sample 132, such that when the confocal microscope 120 focuses on the particular portion of the sample 132 the confocal microscope directs the incident light 103 from the light source 102 to the particular portion of the sample 132 and directs responsive light 105 from the particular portion of the sample 132 to the spectrograph module 140. The confocal microscope 120 may include any filters, apertures, lenses, or other optical elements that are suitable for selectively focusing on any of the plurality of portions of the sample 132.

The sample mount 134 may include any structure suitable for supporting the sample 132 such that the confocal microscope 120 may focus upon the particular portion of the sample 132. The sample mount 134 may be configured for translational movement in any of three independent axes. That is, the sample mount 134 may be configured to align different portions of the sample 132 within the field of view of the confocal microscope 120, and to move the sample 132 away or toward the confocal microscope 120. In another example, the sample mount 134 (and the sample 132) may remain stationary and the confocal microscope 120 may be configured for three-axis positioning relative to the sample mount 134 (and the sample 132). The light guide 116 may be configured to receive the responsive light 105 from the particular portion of the sample 132 via the confocal microscope 120. The light guide 116 may include one or more reflectors or mirrors, however any optical elements configured to redirect the responsive light 105 toward the filter 118A and/or the spectrograph module 140 may be included as part of the light guide 116.

In a typical example, the responsive light 105 may include several portions of light, namely, elastically scattered light, light that is emitted by the sample 132 via Raman scattering, and light that is emitted by the sample 132 via fluorescence or phosphorescence processes. In the context of confocal Raman spectroscopy or confocal fluorescence/phosphorescence spectroscopy, it may be useful to selectively examine the light emitted via Raman scattering or the light emitted via fluorescence or phosphorescence processes because these photophysical processes can be examined to determine characteristics of the sample 132. Accordingly, the filter 118A may be configured to transmit, to the spectrograph module 140, portions of the responsive light 105 emitted by the sample 132 via Raman scattering or fluorescence/phosphorescence processes (e.g., portions of the responsive light 105 having wavelengths that do not correspond to wavelengths of the incident light 103). Such a filter to be used for fluorescence/phosphorescence spectroscopy or Raman spectroscopy might include a notch filter or an edge filter, for example.

The system 100 may also include the filter 118B. The system 100 may be configured so that either the filter 118A or the filter 118B may be aligned to intercept the responsive light 105 before the responsive light 105 is transmitted to the spectrograph module 140. For example, the filters 118A and 118B may be mounted on a wheel that rotates to selectively position one of the filters 118A and 118B (or other filters) in the path of the responsive light 105. As another example, the system 100 may include a simple mount configured to, at any given time, receive one of the filters 118A and 118B (or other filters) and place said filter in the path of the responsive light 105.

In one example, the filter 118A may be suitable for Raman spectroscopy while the filter 118B may be suitable for fluorescence/phosphorescence spectroscopy. For instance, Raman spectroscopy may involve analyzing responsive light 105 that is relatively close in wavelength to the wavelength of the incident light 103. In the context of Raman spectroscopy, it may be useful to detect portions of the responsive light 105 that have undergone small shifts in wavelength because these Stokes-shifted Raman bands may contain information about crystal structure of the sample 132 and vibrational information about atoms within the sample 132. In contrast, fluorescence/phosphorescence spectroscopy may involve analyzing responsive light 105 having much longer wavelengths than that of the incident light 103, because the wavelengths of light emitted by the sample 132 via fluorescence/phosphorescence may be directly representative of excited electronic energy levels excited by the incident light 103.

Figure 2A:
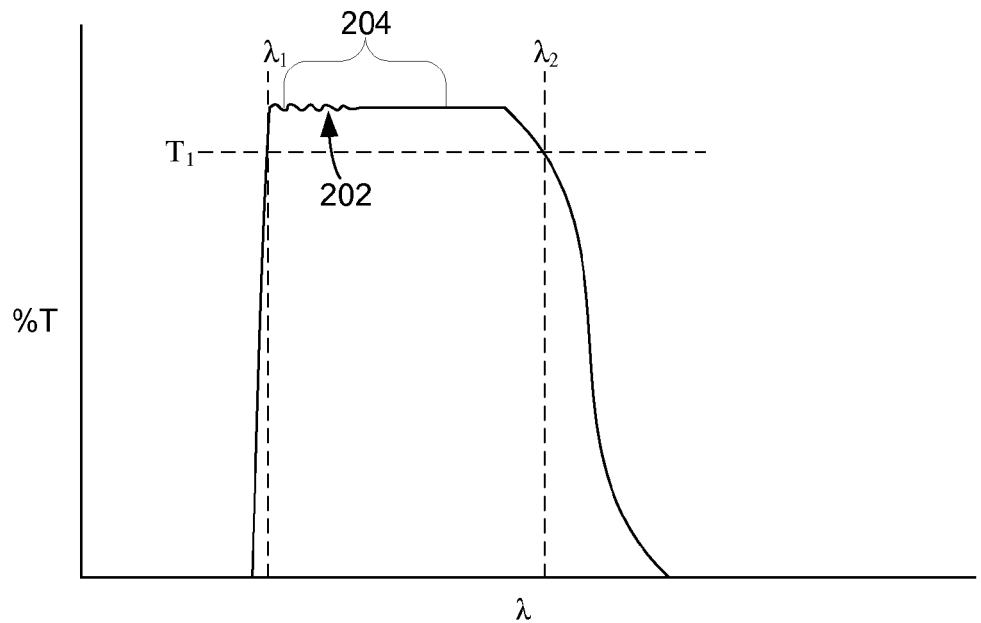
FIG. 2A illustrates an example transmission curve of a filter.

Accordingly, an example transmission curve of the filter 118A is illustrated in FIG. 2A. The horizontal axis of the graph of FIG. 2A corresponds to wavelengths of the responsive light 105 and the vertical axis corresponds to a percentage of the responsive light 105 transmitted by the filter 118A. The filter 118A may have two cutoff wavelengths, namely $\lambda_1$ and $\lambda_2$. The cutoff wavelengths may be wavelengths at which the filter 118A transmits exactly a threshold percentage $T_1$ (e.g., 90%) of light incident upon the filter 118A. The wavelengths greater than or equal to $\lambda_1$ and less than or equal to $\lambda_2$ may be defined as the transmission band of the filter 118A. In one example, $\lambda_1$ may be equal to 460 nm based on the incident light 103 having a wavelength of 455 nm. In this way, the filter 118A may be configured to transmit very little of the wavelengths corresponding to elastic scattering, while transmitting much of the light corresponding to (inelastic) Raman scattering. In one example, $\lambda_2$ may be equal to 900 nm, but other examples are possible.

In some cases, an optical filter will have an undesirable "ripple" characteristic in its transmission curve as shown at ripple 202. The amplitude of the ripple 202 may be proportional to the width of the transmission band of the optical filter (e.g., $|\lambda_1-\lambda_2|$). Therefore, in the context of Raman spectroscopy, where a wavelength range of interest 204 may include wavelengths close in value to the wavelength of the incident light 103, the filter may be designed to reduce the ripple 202 at the expense of the filter having a reduced transmission bandwidth $|\lambda_1-\lambda_2|$. The reduced ripple 202 may lessen discrepancies between intensities of various wavelengths of the responsive light 105 originally scattered by the sample 132 and the (detected) intensities of the various wavelengths transmitted by the filter 118A.

Figure 2B:
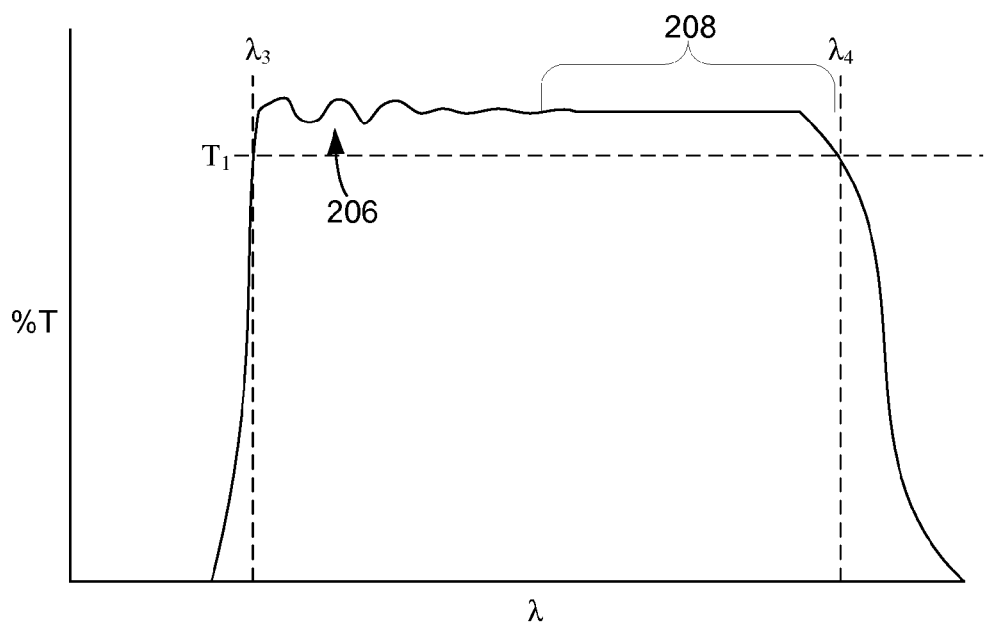
FIG. 2B illustrates another example transmission curve for a filter.

An example transmission curve of the filter 118B is illustrated in FIG. 2B. Similar to FIG. 2A, the horizontal axis of the graph of FIG. 2B corresponds to wavelengths of the responsive light 105 and the vertical axis corresponds to a percentage of light transmitted by the filter 118B. The filter 118B may have two cutoff wavelengths, namely $\lambda_3$ and $\lambda_4$. The cutoff wavelengths may be wavelengths at which the filter 118B transmits exactly a threshold percentage $T_1$ (e.g., 90%) of light incident upon the filter 118B. The wavelengths greater than or equal to $\lambda_3$ and less than or equal to $\lambda_4$ may be defined as the transmission band of the filter 118B. In one example, $\lambda_3$ may be equal to 460 nm which may designed to correspond to a wavelength (e.g., 455 nm) of the incident light 103. In this way, the filter 118B may be configured to transmit very little of the wavelengths corresponding to elastic scattering, while transmitting much of the light corresponding to fluorescence or phosphorescence spectra. In one example, $\lambda_4$ may be equal to 1050 nm, but other examples are possible.

As described above, an optical filter may have an undesirable "ripple" characteristic in its transmission curve as shown at ripple 206. The amplitude of the ripple 206 may be proportional to the width of the transmission band of the optical filter (e.g., $|\lambda_3-\lambda_4|$). Therefore, in the context of fluorescence/phosphorescence spectroscopy, where the wavelength range of interest 208 may include wavelengths closer in value to the cutoff wavelength $\lambda_4$ than the cutoff wavelength $\lambda_3$, the filter 118B may be designed to have a wide transmission bandwidth $|\lambda_3-\lambda_4|$ at the expense of an increased ripple 206.

Returning to FIG. 1, the light guide 142 may be configured to receive the responsive light 105 from the filter 118A or the filter 118B, depending on which filter is positioned in the path of the responsive light 105. The light guide 142 may include one or more reflectors or mirrors, however any optical elements configured to redirect the responsive light 105 toward the diffraction grating 146A (or 146 B) may be included as part of the light guide 142.

The grating mount 148 may include any structure suitable for supporting the diffraction grating 146A (or 146B) so that the diffraction grating 146A (or 146B) is in the path of the responsive light 105. For example, the grating mount 148 may include a set of magnetic mounts, or an adhesive base that is configured to hold the diffraction grating 146A (or 146B), or may include one or more spring loaded clips that hold the diffraction grating 146A (or 146B) in place. Other examples are possible.

Figure 3A:
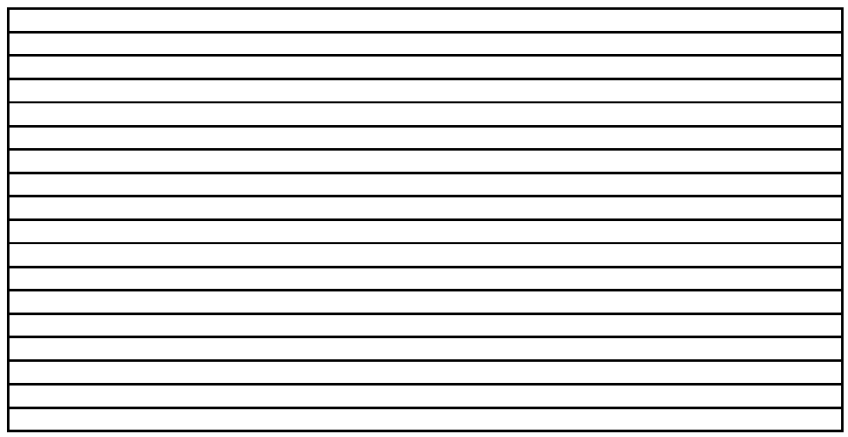
FIG. 3A illustrates an example diffraction grating.

The diffraction grating 146A is illustrated in FIG. 3A. The diffraction grating 146A may be a periodic structure made of metal, plastic, graphite, or any material suitable for diffracting light. The diffraction grating 146A may include a periodic array of grooves or other structures configured to scatter light and cause constructive and/or destructive interference as the scattered light propagates. In one example, the periodicity of the diffraction grating 146A may be defined by a line density greater than or equal to 775 lines/millimeter (mm) and less than or equal to 905 lines/mm. That is, for a line density of 800 lines/mm, the structure of the diffraction grating 146A may repeat itself 800 times within every 1 mm.

Figure 3B:
FIG. 3B illustrates another example diffraction grating.

The diffraction grating 146B is illustrated in FIG. 3B. The diffraction grating 146B may be similar in structure to the diffraction grating 146A or be made of any material that makes up the diffraction grating 146A. In one example, the periodicity of the diffraction grating 146B may be defined by a line density greater than or equal to 125 lines/mm and less than or equal to 175 lines/mm. More specifically, the line density of the diffraction grating 146B may be substantially equal to 150 lines/mm.

Returning to FIG. 1, depending on the configuration of the system 100, either the diffraction grating 146A or 146B may be configured to disperse the responsive light 105 according to wavelength, so that the light sensor 150 may detect various wavelengths of the responsive light 105.

The light guide 144 may be configured to receive the dispersed responsive light 105 from the diffraction grating 146A (or 146B). The light guide 144 may include one or more reflectors or mirrors, however any optical elements configured to redirect the dispersed responsive light 105 toward the light sensor 150 may be included as part of the light guide 144.

In addition, the diffraction grating 146A which disperses the responsive light 105 may be comprised of reflective grating(s) as shown in FIG. 1 or may be comprised of transmissive gratings such as volume holographic gratings.

As examples, the light sensor 150 may include a charge-coupled device (CCD) image sensor or a complimentary metal-oxide semiconductor (CMOS) image sensor. However, the light sensor 150 may include any element configured to sense intensity of light and distinguish between wavelengths of light over a two dimensional surface.

Figure 4:
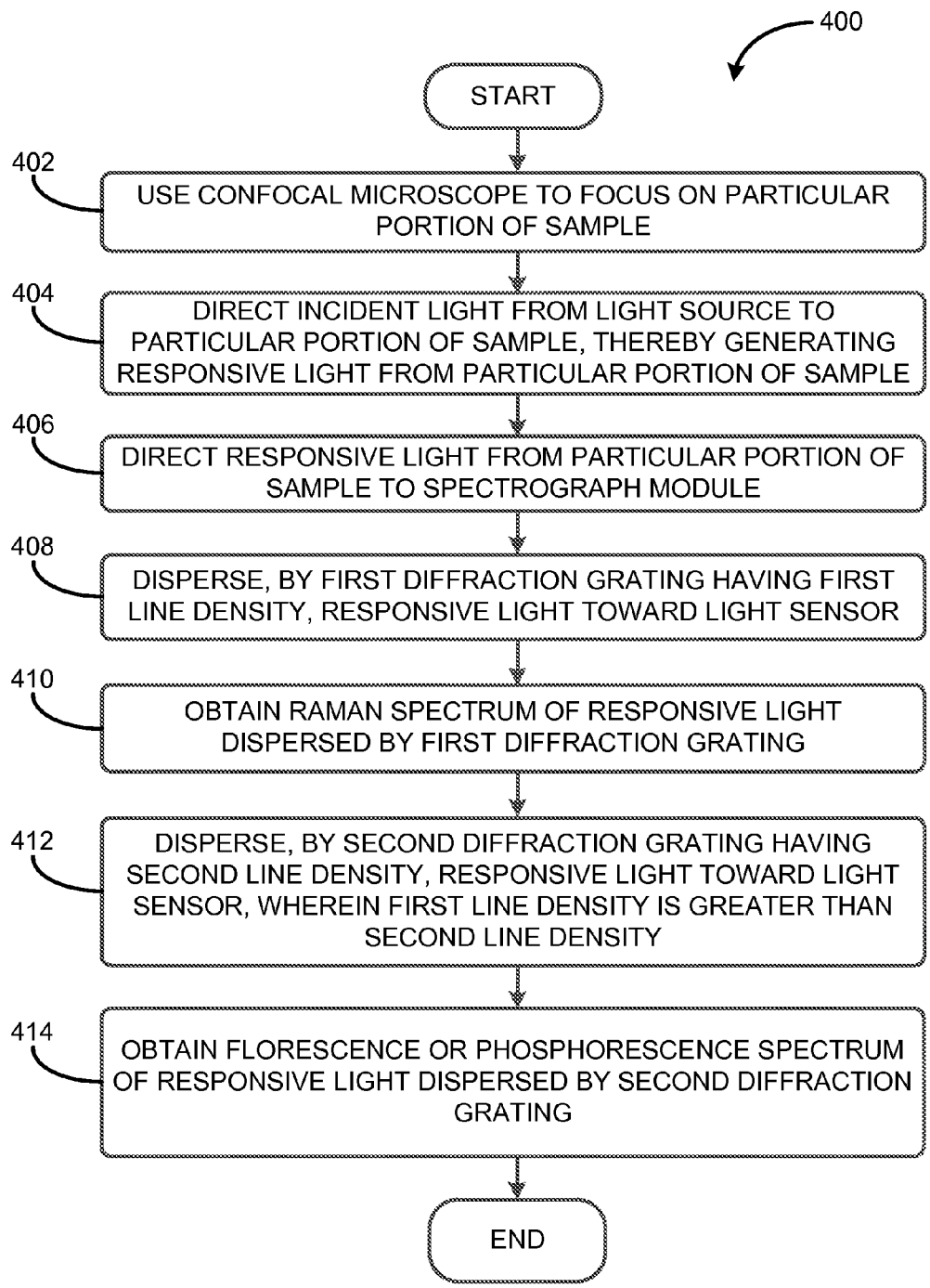
FIG. 4 is a block diagram of an example method.

FIG. 4 is a block diagram of an example method 400. Method 400 may include one or more functions as illustrated by blocks 402-414. Although the blocks are illustrated in a sequential order, these blocks may in some instances be performed in parallel, and/or in a different order than those described herein. Also, the various blocks may be combined into fewer blocks, divided into additional blocks, and/or removed based on the desired implementation.

In addition, for the method 400 and other processes and methods disclosed herein, FIG. 4 shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a non-transitory computer readable medium, for example, such as computer-readable media that stores data for short periods of time like register memory, processor cache, and random access memory (RAM). The computer readable medium may also include non-transitory media, such as secondary or persistent long term storage, like read-only memory (ROM), optical or magnetic disks, or compact-disc read-only memory (CD-ROM), for example. The computer readable media may also be any other volatile or non-volatile storage system. The computer readable medium may be considered a computer readable storage medium, a tangible storage device, or other article of manufacture, for example. In addition, for the method 400 and other processes and methods disclosed herein, each block in FIG. 4 may represent circuitry that is configured to perform the specific logical functions of the method 400.

At block 402, the method 400 involves using a confocal microscope to focus on a particular portion of a sample. For example, the confocal microscope 120 of FIG. 1 may be used to focus on a particular portion of the sample 132.

At block 404, the method 400 involves directing, via the confocal microscope, incident light from a light source to the particular portion of the sample, thereby generating responsive light from the particular portion of the sample. For example, the confocal microscope 120 may direct the incident light 103 from the light source 102 to the particular portion of the sample 132, thereby generating responsive light 105 from the particular portion of the sample 132. In one example, the incident light has a wavelength substantially equal to 455 nm.

At block 406, the method 400 involves directing, via the confocal microscope, the responsive light from the particular portion of the sample to a spectrograph module. The spectrograph module comprises a light sensor and a mount configured to receive any of a plurality of different diffraction gratings having different line densities. For example, the confocal microscope may direct the responsive light 105 from the particular portion of the sample 132 to the spectrograph module 140.

At block 408, the method 400 involves dispersing, by a first diffraction grating having a first line density, the responsive light toward the light sensor. For example, the diffraction grating 146A (e.g., having a line density greater than or equal to 775 lines/mm and less than or equal to 905 lines/mm) may disperse the responsive light 105 toward the light sensor 150.

At block 410, the method 400 involves obtaining, by the spectrograph module, a Raman spectrum of the responsive light dispersed by the first diffraction grating. For example, the spectrograph module 140 may obtain a Raman spectrum of the responsive light 105 that is dispersed by the diffraction grating 146A.

At block 412, the method 400 involves dispersing, by a second diffraction grating having a second line density, the responsive light toward the light sensor. The first line density is greater than the second line density. For example, the diffraction grating 146B may disperse the responsive light 105 toward the light sensor 150. In various examples, the second line density may be greater than or equal to 125 lines/mm and less than or equal to 175 lines/mm, or more specifically, substantially equal to 150 lines/mm.

At block 414, the method 400 involves obtaining, by the spectrograph module, a fluorescence or phosphorescence spectrum of the responsive light dispersed by the second diffraction grating. For example, the spectrograph module 140 may obtain a fluorescence or phosphorescence spectrum of the responsive light 105 that is dispersed by the diffraction grating 146B (after the diffraction grating 146B has been configured to be in the path of the responsive light 105).

Further functions related to the method 400 may include transmitting, by a first filter, at least a threshold percentage of the responsive light having wavelengths corresponding to a first transmission band of the first filter. In this context, obtaining the Raman spectrum of the responsive light may include obtaining a Raman spectrum of the responsive light that is transmitted by the first filter.

For example, the filter 118A may transmit at least a threshold percentage (e.g., 90%) of the responsive light 105 having wavelengths corresponding to the transmission band of the filter 118A. Purely by way of example, the transmission band of the filter 118A may include any wavelength greater than or equal to 460 nm and less than or equal to 900 nm. The light transmitted by the filter 118A may be transmitted to the spectrograph module 140.

Further functions related to the method 400 may include transmitting, by a second filter, at least a threshold percentage of the responsive light having wavelengths corresponding to a second transmission band of the second filter. The second transmission band may include wavelengths that are greater than any wavelength of the first transmission band.

In this context, obtaining the fluorescence or phosphorescence spectrum of the responsive light may include obtaining a fluorescence or phosphorescence spectrum of the responsive light that is transmitted by the second filter.

For example, the filter 118B (when positioned in the path the responsive light 105) may transmit at least a threshold percentage (e.g., 90%) of the responsive light 105 having wavelengths corresponding to the transmission band of the filter 118B. For instance, the transmission band of the filter 118B may include any wavelength greater than or equal to 460 nm and less than or equal to 1050 nm. The light transmitted by the filter 118B may be transmitted to the spectrograph module 140.

As an example, the system 100 may be operated in a first mode, where the filter 118A and the diffraction grating 146A are positioned to be in the path of the responsive light 105. By using the first mode, a Raman spectrum of the particular portion of the sample 132 may be obtained by the system 100. Next, the system 100 may be configured to operate in a second mode, where the filter 118B and the diffraction grating 146B are positioned to be in the path of the responsive light 105. Then, by operating in the second mode, a fluorescence or phosphorescence spectrum of the sample 132 may be obtained by the system 100. Alternatively, the system 100 may be used to obtain a fluorescence or phosphorescence spectrum of the sample 132 by operating in the second mode and then be configured to operate in the first mode to obtain a Raman spectrum of the sample 132.

In another example, the confocal microscope 120 may be configured to scan a plurality of portions of the sample 132, obtaining a Raman spectra for each of the plurality of portions. Also, the confocal microscope 120 may be configured to scan the same plurality of portions of the sample 132, obtaining a fluorescence or phosphorescence spectrum for each of the plurality of portions. Obtaining a Raman spectrum for the plurality of portions may be performed before or after obtaining the fluorescence or phosphorescence spectrum for the plurality of portions.

The above detailed description describes various features and functions of the disclosed systems and methods with reference to the accompanying figures. While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the following claims.

The invention claimed is:

1. A system comprising:
a light source configured to emit incident light;
a first diffraction grating having a first line density;
a second diffraction grating having a second line density, wherein the first line density is greater than the second line density;
a spectrograph module comprising a light sensor and a mount configured to (i) receive the first diffraction grating to provide a first mode of operation and (ii) to receive the second diffraction grating to provide a second mode of operation;
a confocal microscope optically coupled to the light source and the spectrograph module, wherein the confocal microscope is operable to selectively focus on any of a plurality of portions of a sample, such that when the confocal microscope focuses on a particular portion of the sample the confocal microscope directs the incident light from the light source to the particular portion of the sample and directs responsive light from the particular portion of the sample to the spectrograph module,
a first filter configured to transmit, for any wavelength of a first transmission band, at least a threshold percentage of the responsive light incident upon the first filter, wherein in the first mode of operation the spectrograph module is operable to obtain a Raman spectrum of the responsive light using the first filter; and
a second filter configured to transmit, for any wavelength of a second transmission band, at least the threshold percentage of the responsive light incident upon the second filter, wherein the second transmission band includes wavelengths greater than any wavelength of the first transmission band, wherein a lower cutoff wavelength of the first transmission band is substantially equal to a lower cutoff wavelength of the second transmission band, and wherein in the second mode of operation the spectrograph module is operable to obtain a fluorescence or phosphorescence spectrum of the responsive light using the second filter; and
wherein in the first mode of operation the spectrograph module is operable to obtain a Raman spectrum of the responsive light using the first diffraction grating and in the second mode of operation the spectrograph module is operable to obtain a fluorescence or phosphorescence spectrum of the responsive light using the second diffraction grating.

2. The system of claim 1, wherein the incident light has a wavelength that is substantially equal to 455 nanometers.

3. The system of claim 1, wherein the second line density is substantially equal to 150 lines per millimeter.

4. The system of claim 1, wherein the threshold percentage is at least 90 percent.

5. The system of claim 1, wherein the second transmission band includes all wavelengths greater than or equal to 460 nanometers and less than or equal to 1050 nanometers.

6. The system of claim 1, wherein the first line density is greater than or equal to 775 lines per millimeter and less than or equal to 905 lines per millimeter.

7. The system of claim 1, wherein the second line density is greater than or equal to 125 lines per millimeter and less than or equal to 175 lines per millimeter.

8. A method comprising:
using a confocal microscope to focus on a particular portion of a sample;
directing, via the confocal microscope, incident light from a light source to the particular portion of the sample, thereby generating responsive light from the particular portion of the sample;
transmitting, by a first filter, at least a threshold percentage of the responsive light having wavelengths corresponding to a first transmission band of the first filter;
directing, via the confocal microscope, the responsive light transmitted by the first filter from the particular portion of the sample to a spectrograph module, wherein the spectrograph module comprises a light sensor and a mount configured to receive any of a plurality of different diffraction gratings having different respective line densities;
dispersing, by a first diffraction grating having a first line density, the responsive light transmitted by the first filter toward the light sensor;

obtaining, by the spectrograph module, a Raman spectrum of the responsive light dispersed by the first diffraction grating and transmitted by the first filter;

transmitting, by a second filter, at least a threshold percentage of the responsive light having wavelengths corresponding to a second transmission band of the second filter, wherein the second transmission band includes wavelengths that are greater than any wavelength of the first transmission band, and wherein a lower cutoff wavelength of the first transmission band is substantially equal to a lower cutoff wavelength of the second transmission band;

directing, via the confocal microscope, the responsive light transmitted by the second filter from the particular portion of the sample to the spectrograph module;

dispersing, by a second diffraction grating having a second line density, the responsive light transmitted by the second filter toward the light sensor, wherein the first line density is greater than the second line density; and obtaining, by the spectrograph module, a fluorescence or phosphorescence spectrum of the responsive light dispersed by the second diffraction grating and transmitted by the second filter.

9. The method of claim 8, wherein the incident light has a wavelength that is substantially equal to 455 nanometers.

10. The method of claim 8, wherein the second line density is substantially equal to 150 lines per millimeter.

11. The method of claim 8, wherein the second transmission band includes all wavelengths greater than or equal to 460 nanometers and less than or equal to 1050 nanometers.

12. The method of claim 8, wherein the first line density is greater than or equal to 775 lines per millimeter and less than or equal to 905 lines per millimeter.

13. The method of claim 8, wherein the second line density is greater than or equal to 125 lines per millimeter and less than or equal to 175 lines per millimeter.

* * * * *